(12) United States Patent
King et al.

(10) Patent No.: US 10,282,975 B2
(45) Date of Patent: May 7, 2019

(54) CARBON MONOXIDE ALARM SUPERVISION

(71) Applicant: Microchip Technology Incorporated, Chandler, AZ (US)

(72) Inventors: William King, Jeffersonville, PA (US); Jonathan Corbett, Havertown, PA (US); Erik Johnson, Wyndmoor, PA (US)

(73) Assignee: MICROCHIP TECHNOLOGY INCORPORATED, Chandler, AZ (US)

( * ) Notice: Subject to any disclaimer, the term of this patent is extended or adjusted under 35 U.S.C. 154(b) by 0 days.

(21) Appl. No.: 16/043,667

(22) Filed: Jul. 24, 2018

(65) Prior Publication Data

US 2019/0051145 A1    Feb. 14, 2019

Related U.S. Application Data

(60) Provisional application No. 62/542,482, filed on Aug. 8, 2017.

(51) Int. Cl.
| | |
|---|---|
| *G01N 33/00* | (2006.01) |
| *G08B 21/14* | (2006.01) |
| *G08B 29/14* | (2006.01) |
| *G01N 27/416* | (2006.01) |

(52) U.S. Cl.
CPC ........ *G08B 29/14* (2013.01); *G01N 27/4163* (2013.01); *G01N 33/004* (2013.01); *G01N 33/007* (2013.01); *G08B 21/14* (2013.01)

(58) Field of Classification Search
CPC ........ G08B 29/14; G08B 17/10; G08B 21/14; G08B 21/18; G08B 17/117; G08B 21/182; G01N 27/4163; G01N 33/004; G01N 33/007
See application file for complete search history.

(56) References Cited

U.S. PATENT DOCUMENTS

| | | | |
|---|---|---|---|
| 4,390,869 A | 6/1983 | Christen et al. | 340/632 |
| 5,886,638 A | 3/1999 | Tanguay | 340/632 |

FOREIGN PATENT DOCUMENTS

| | | | |
|---|---|---|---|
| JP | 2010266355 A | 11/2010 | G01N 27/26 |
| WO | 02/15137 A1 | 2/2002 | G08B 17/10 |

OTHER PUBLICATIONS

Barrettino, Diego et al., "CMOS Monolithic Metal—Oxide Gas Sensor Microsystems," IEEE Sensors Journla, vol. 6, No. 2, pp. 276-286, Apr. 1, 2006.
International Search Report and Written Opinion, Application No. PCT/US2018/044536, 12 pages, Oct. 9, 2018.

*Primary Examiner* — Omeed Alizada
(74) *Attorney, Agent, or Firm* — Slayden Grubert Beard PLLC

(57) ABSTRACT

Supervision and testing of a carbon monoxide (CO) alarm using an application specific integrated circuit (ASIC) and microcontroller. Wherein an electrochemical CO sensor is isolated from its detection circuit and a voltage charge is changed thereon then the CO sensor is reconnected to the detection circuit, wherein the voltage charge on the CO sensor returns to an equilibrium state over time. From the voltage versus time results a determination is made as to whether the CO sensor and CO detection circuit are functioning properly. All test and control circuits may be provided by the ASIC.

10 Claims, 4 Drawing Sheets

CARBON MONOXIDE ALARM SUPERVISION

RELATED PATENT APPLICATION

This application claims priority to commonly owned U.S. Provisional Patent Application No. 62/542,482; filed Aug. 8, 2017; which is hereby incorporated by reference herein for all purposes.

TECHNICAL FIELD

The present disclosure relates to carbon monoxide detection and, in particular, to carbon monoxide (CO) alarm supervision.

BACKGROUND

Underwriters Laboratories (UL) has a standard for single and multiple station carbon monoxide alarms, UL-2034. In this UL standard there is a requirement to supervise the operational condition of the carbon monoxide (CO) alarm as outlined the UL-2034, paragraph 38.1.1. To meet this standard, some present technology CO alarms require the use of external components to isolate the CO alarm detection amplifier. Furthermore, other CO alarm supervision solutions are limited to only creating current sinks. Also, other solutions may require a significant period of time to operate while waiting for the output of the CO detection circuitry to come back into equilibrium. This could be multiple seconds, or even as much as 10-15 seconds for a complete diagnosis of the CO alarm circuitry.

SUMMARY

Therefore, what is needed are better, faster and lower cost solutions for carbon monoxide alarm supervision.

According to an embodiment, a method for carbon monoxide alarm supervision may comprise the steps of: decoupling an electrochemical carbon monoxide sensor from a carbon monoxide operation amplifier; changing a voltage charge on the electrochemical carbon monoxide sensor using a current source or sink; recoupling the carbon monoxide operation amplifier to the electrochemical carbon monoxide sensor; measuring voltage on an output of the carbon monoxide operation amplifier until it does not substantially change; evaluating time elapsed until the voltage does not substantially change; and determining from the time elapsed whether the carbon monoxide sensor and the operation amplifier circuits may be working.

According to a further embodiment of the method, may comprise the step of determining whether a voltage charge on the electrochemical carbon monoxide sensor may be within an expected range. According to a further embodiment of the method, may comprise the steps of: storing the measured voltages and times thereof in a memory; and evaluating a time-voltage profile thereof for carbon monoxide alarm supervision.

According to a further embodiment of the method, the step of determining whether the voltage charge on the electrochemical carbon monoxide sensor may be within the expected range may comprise the steps of: measuring the voltage charge across inputs of the carbon monoxide operation amplifier coupled to the electrochemical carbon monoxide sensor; and comparing the measured voltage charge to the expected range.

According to another embodiment, a method for carbon monoxide alarm supervision may comprise the steps of: measuring and storing in a memory an initial voltage from an output of a carbon monoxide operation amplifier; decoupling an electrochemical carbon monoxide sensor from the carbon monoxide operation amplifier; changing a voltage charge on the electrochemical carbon monoxide sensor using a current source or sink; recoupling the carbon monoxide operation amplifier to the electrochemical carbon monoxide sensor; comparing voltages on the output of the carbon monoxide operation amplifier with the stored initial voltage; determining a time until a first one of the voltages on the output of the carbon monoxide operation may be about equal to the initial voltage; and determining from the time whether the carbon monoxide sensor and the operation amplifier circuits may be working.

According to a further embodiment of the method, may comprise the step of determining whether a voltage charge on the electrochemical carbon monoxide sensor may be within an expected range. According to a further embodiment of the method, may comprising the steps of: storing the voltages on the output of the carbon monoxide operation amplifier and times thereof in a memory; and evaluating a time-voltage profile thereof for carbon monoxide alarm supervision.

According to a further embodiment of the method, the step of determining whether the voltage charge on the electrochemical carbon monoxide sensor may be within the expected range may comprise the steps of: measuring the voltage charge across inputs of the carbon monoxide operation amplifier coupled to the electrochemical carbon monoxide sensor; and comparing the measured voltage charge to the expected range.

According to yet another embodiment, a carbon monoxide alarm having supervision may comprise: an electrochemical carbon monoxide sensor having first and second terminals; an operational amplifier having first and second inputs coupled to the first and second terminals, respectively, of the electrochemical carbon monoxide sensor, wherein the operational amplifier has an output that can be enabled and disabled, whereby when the output may be disabled it may be at a high impedance; a voltage reference having an output coupled to the first terminal of the electrochemical carbon monoxide sensor and the first input of the operational amplifier; a feedback resistor coupled between the output and second input of the operational amplifier; a first current source or sink coupled to the first terminal of the electrochemical carbon monoxide sensor and the first input of the operational amplifier for charging or discharging the electrochemical carbon monoxide sensor, wherein the first current source or sink output can be disabled and enabled; a multiplexer having inputs coupled to the first and second inputs and the output of the operational amplifier, and an output adapted for coupling to a first analog input of a microcontroller; the output of the operational amplifier may be coupled to a second analog input of the microcontroller; a supervisor alarm controller having control outputs coupled to the multiplexer, operation amplifier and current source, and an input coupled to the microcontroller; wherein during testing of the carbon monoxide alarm the operational amplifier may be disabled, and the first current source or sink may be enabled, whereby the output of the operational amplifier may provide a voltage to the microcontroller that may be representative of a voltage charge between the first and second terminals of the electrochemical carbon monoxide sensor while the voltage charge reaching equilibrium; and during normal carbon monoxide monitoring the operational amplifier may be enabled, and the first current source or sink may be disabled, whereby the output of the operational amplifier provides a voltage to the microcontroller that may be representative of a voltage charge between the first and second terminals of the electrochemical carbon monoxide sensor.

According to a further embodiment, a second current sink or source may be coupled to the second terminal of the electrochemical carbon monoxide sensor and the second input of the operational amplifier for discharging or charging the electrochemical carbon monoxide sensor, wherein the second current sink or source output may be disabled and enabled. According to a further embodiment, a microcontroller may control the first current source or sink, the multiplexer and the supervisor alarm controller. According to a further embodiment, a memory with the microcontroller may store voltage and time values.

According to a further embodiment, an application specific integrated circuit (ASIC) may comprise the operational amplifier, the voltage reference, the first current source or sink, and the multiplexer. According to a further embodiment, the microcontroller may comprise the operational amplifier, the voltage reference, the first current source or sink, and the multiplexer. According to a further embodiment, the operational amplifier may comprise a tri-state circuit for enabling and disabling the output thereof. According to a further embodiment, the operational amplifier may comprise an open collector circuit for enabling and disabling the output thereof. According to a further embodiment, may comprise a switch coupled between the operational amplifier and the feedback resistor and the multiplexer for enabling and disabling the output thereof. According to a further embodiment, the switch may be controlled by the supervisor alarm controller.

BRIEF DESCRIPTION OF THE DRAWINGS

A more complete understanding of the present disclosure may be acquired by referring to the following description taken in conjunction with the accompanying drawings wherein.

Figure 1:
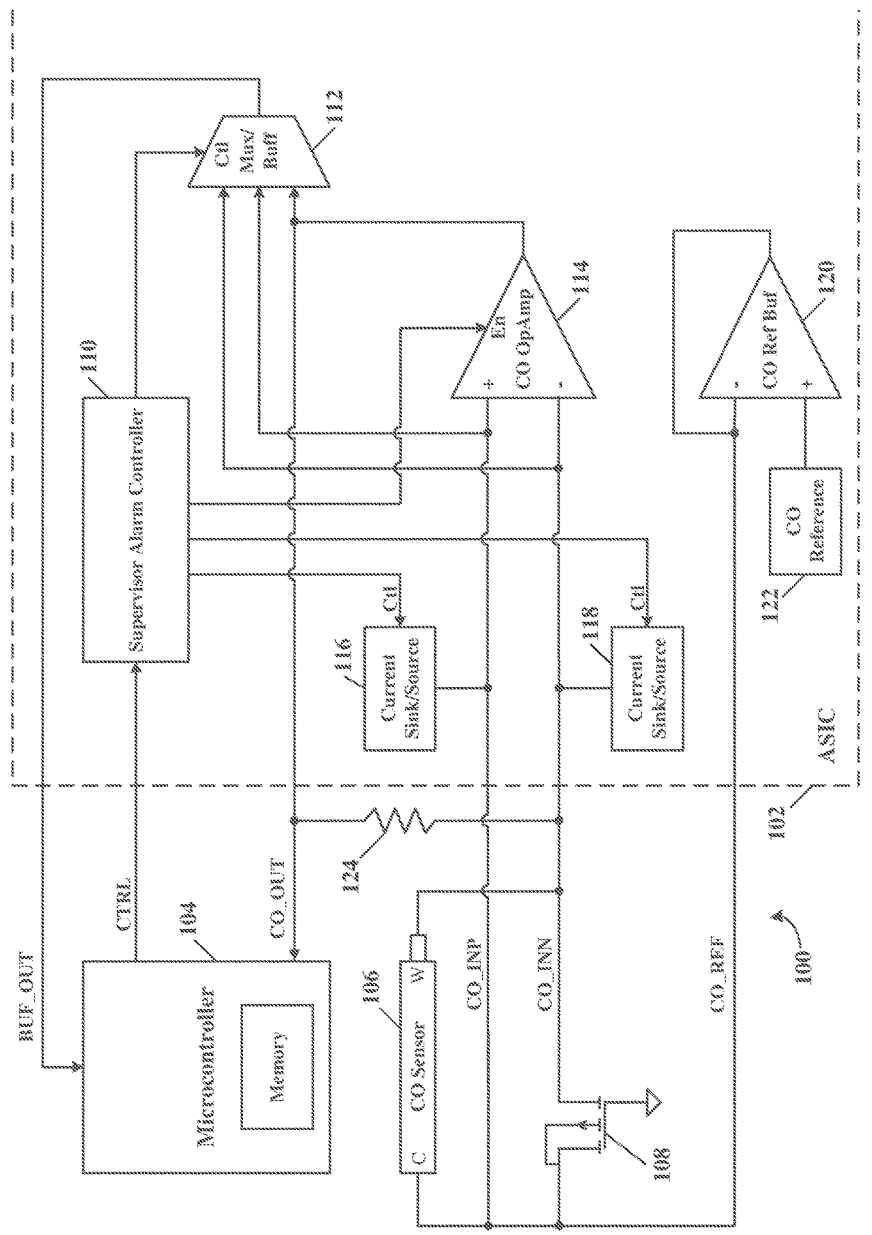
FIG. 1 illustrates a schematic block diagram of a carbon monoxide detector having microcontroller alarm supervision, according to a specific example embodiment of this disclosure.

While the present disclosure is susceptible to various modifications and alternative forms, specific example embodiments thereof have been shown in the drawings and are herein described in detail. It should be understood, however, that the description herein of specific example embodiments is not intended to limit the disclosure to the forms disclosed herein.

DETAILED DESCRIPTION

Embodiments of the present disclosure include systems and methods to diagnosis several common failure modes in carbon monoxide (CO) sensors, detectors, alarms, and monitors. The failure modes may arise due to breakage of wires, components, or foreign object damage. The failures may also be caused by a short circuit in a component and/or printed circuit board conductor. Embodiments of the present disclosure may also include systems and methods for characterizing overall condition and health of CO sensors, detectors, alarms, and monitors. The Embodiments of the present disclosure may be used to meet the requirements of UL-2034, paragraph 38.1.1.

Embodiments of the present disclosure may diagnose a CO sensor's health or status by selectively sourcing or sinking current to/from the CO sensor. Moreover, embodiments of the present disclosure may be configured to tristate the output of an operational amplifier(s) associated with the CO sensor. In addition, embodiments of the present disclosure may be configured to monitor inputs to the operational amplifier(s) associated with the CO sensor during diagnostic checks. This may provide a faster method to quantify CO sensor health and performance.

Embodiments of the present disclosure may be implemented with an integrated circuit on-chip test feature. The feature may allow the isolation of a CO operational amplifier from an external CO sensor. From this, a self-diagnostic test may be performed. The on-chip feature may be embedded within a mixed signal (analog and digital) integrated circuit, e.g., microcontroller, application specific integrated circuit (ASIC), etc., hereinafter referred to as a "microcontroller." A test sequence for testing the CO sensor and alarm may be implemented with the microcontroller. The test sequence may be customizable. Furthermore, this feature and others may be accessed with any suitable bus, such as, for example but is not limited to, a serial peripheral interface (SPI) bus. Test voltages used in the testing of the CO alarm may be buffered.

Embodiments of the present disclosure may include altering the voltage charge on the electrochemical CO sensor. Altering the voltage charge may be performed with an on-chip current source or sink. Subsequently, the re-establishment of equilibrium operation of the CO sensor may be characterized. The characterization may illustrate the health or status of the CO sensor. Embodiments of the present disclosure may internally isolate the feedback path of the CO operational amplifier(s) while charging or discharging current is applied to the CO sensor. The feedback path may then be re-established to allow for voltage charge equilibrium of the CO sensor to be restored. The voltages at the inputs of the CO operational amplifier may be measured during application of the charging or discharging current (CO operational amplifier output disabled). The voltages at the inputs and the output of the CO operational amplifier (output enabled) may then be measured during voltage charge equilibrium restoration of the electrochemical CO sensor.

By isolating the output, e.g., tristate, of the CO operational amplifier and then altering the charge balance of the CO sensor with an internal current sink or source, the system may check the condition of the CO sensor and its associated circuitry. While altering this charge balance it is possible to monitor the change in voltage across the CO sensor terminals with respect to the charge/discharge time of the CO sensor's capacitance to reach voltage equilibrium, which may be measured at the inputs of the CO operational amplifier. The return time to reach capacitance voltage equilibrium is a function of both the sensor's health as well as the circuit's inter-connectivity and provides a characteristic signature of the CO detection circuit performance. It is contemplated and within the scope of this disclosure that a switch (not shown in FIG. 1), e.g., FET switch, may be used to isolate the output of the CO operational amplifier.

After the charge balance on the CO sensor has been altered, then by re-enabling the CO operational amplifier the CO detection circuit will re-establish charge balance over time. This re-establishment of charge balance over time will be observable in the output performance of the CO operational amplifier. Therefore, the output performance of the CO operational amplifier may be evaluated over time to characterize the health of the CO sensor and detection circuit. Additionally, the inputs of the CO operational amplifier may also be evaluated during this time (voltage charge on the CO sensor).

Referring now to the drawings, the details of example embodiments are schematically illustrated. Like elements in the drawings will be represented by like numbers, and similar elements will be represented by like numbers with a different lower-case letter suffix.

Referring now to FIG. 1, depicted is a schematic block diagram of a carbon monoxide detector having microcontroller alarm supervision, according to a specific example embodiment of this disclosure. A carbon monoxide detector having microcontroller alarm supervision, generally represented by the numeral 100, may comprise a microcontroller with memory 104, a carbon monoxide (CO) sensor 106, an anti-polarization transistor 108, a supervisor alarm controller 110, a multiplexer and buffer 112, a carbon monoxide operational amplifier 114, a current source/sink 116, a current source/sink 118, a buffer amplifier 120, a voltage reference 122, and a feedback resistor 124. An application specific integrated circuit (ASIC) 102 (or similar) may be configured to provide the supervisor alarm controller 110, multiplexer and buffer 112, carbon monoxide operational amplifier 114, current source/sink 116, current source/sink 118, buffer amplifier 120, and voltage reference 122. It is contemplated and within the scope of this disclosure that the functions of the ASIC 102 may be included as part of the microcontroller 104 and configured in one integrated circuit package.

The supervisor alarm controller 110 receives instructions from the microcontroller 104 over a control bus (CTRL), for example but is not limited to, a serial peripheral interface (SPI). With these instructions it may control the multiplexer and buffer 112, carbon monoxide operational amplifier 114, current source/sink 116, and current source/sink 118. The output of the CO operational amplifier 114 may be enabled or put into a high impedance state, e.g., tristate, open collector-unasserted, with a switch, etc., effectively disconnecting the output from the circuit. The current sources/sinks 116 and 118 may be enabled or disabled, and when enabled the current value(s) thereof may be programmed. Outputs of the current sources/sinks 116 and 118 may be controlled in a similar fashion as the output of the CO operational amplifier 114. The current sources/sinks 116 and/or 118 may be used to increase or decrease the voltage charge on the CO sensor 106.

The multiplexer and buffer 112 selectively couples and buffers voltages at the output and inputs of the operational amplifier 114 to an analog input (BUF_OUT) of the microcontroller 104. The output of the operational amplifier 114 is also coupled to another analog input (CO_OUT) of the microcontroller 104.

The voltage reference 122 provides a voltage reference for the CO sensor 106 and is buffered by the buffer amplifier 120 having an output coupled to the counter (C) terminal of the CO sensor 106. The CO sensor 106 may be an electrochemical CO sensor which is capacitive and retains a voltage charge that may change when CO gas is detected. The change in voltage charge on the CO sensor 106 is coupled to and amplified by the CO operational amplifier 114. Electrochemical CO sensors may be, for example but are not limited to, Figaro models TGS5042, TGS5141 and the like.

During normal operation of the carbon monoxide detector 100, the voltage charge on the CO sensor 106 is in an equilibrium state as represented by a certain voltage on the output of the CO operational amplifier 114. This equilibrium output voltage is coupled to the analog input (CO_OUT) of the microcontroller 104, wherein a sufficient change in the voltage thereof may represent a CO gas detection event. The CO operational amplifier 114 is configured as a standard differential input operation amplifier having a gain setting feedback resistor 124. An anti-polarization transistor 108 may also be coupled in parallel with the differential inputs of the CO operational amplifier 114 and working (C and W) terminals of the CO sensor 106. The current sources/sinks 116 and 118 are effectively decoupled from the CO detection circuit during normal operation thereof.

During test mode(s) operation of the carbon monoxide detector 100, the output of the CO operational amplifier 114 may be disabled and put into a high impedance state, effectively decoupling the operational amplifier 114 from the CO detection circuit. The inputs of the operational amplifier 114 are high impedance so substantially no loading of the circuit voltages result therefrom. During testing when the current source/sink 116 is enabled as a current source, charging current may be injected into the C terminal of the CO sensor 106, effectively raising the voltage at the C terminal in relation to the voltage at the W terminal thereof. When the current source/sink 118 is enabled as a current sink, a discharging current may be removed from the W terminal of the CO sensor 106, effectively decreasing the voltage at the W terminal in relation to the voltage at the C terminal. The source and sink configurations of current sources/sinks 116 and 118 may be reversed so as to effectively decrease the voltage at the C terminal and/or increase the voltage at the W terminal. Configuration and operation of the current sources/sinks 116 and 118 may be controlled through the supervisor alarm controller 110 receiving control signals (CTRL) from the microcontroller 104, e.g., via a serial SPI bus.

Voltages on the C and W terminals of the CO sensor 106 may be monitored by the microcontroller 104 over time. The C and W terminal voltages may be monitored when the CO operational amplifier 114 output is disabled and then when it is re-enabled. When the current source/sink 116 or current source/sink 118 is disabled (decoupled) and the CO operational amplifier 114 output is re-enabled, then the voltage charge on the CO sensor 106 will re-equalize over time. A voltage versus time table(s) may be implemented in a memory (not shown) of the microcontroller 104 and used for verification of the proper operation of the CO sensor 106 and overall operation of the carbon monoxide detector 100.

Figure 2:
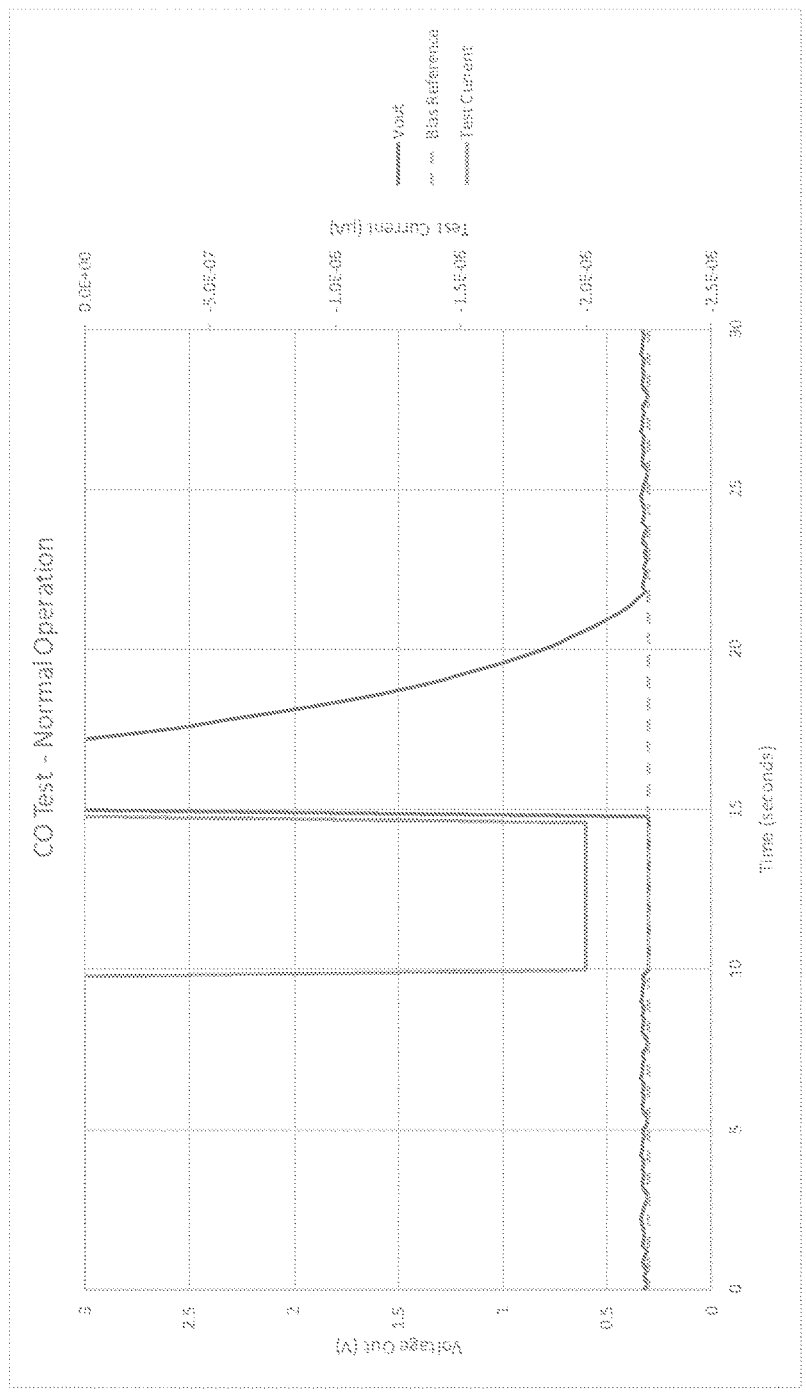
FIG. 2 illustrates a schematic voltage versus time graph of an operational test of the carbon monoxide detector showing normal operation thereof, according to the teachings of this disclosure.

Referring now to FIG. 2, depicted is a schematic voltage versus time graph of an operational test of the carbon monoxide detector showing normal operation thereof, according to the teachings of this disclosure. A sink current pulse is applied for about five (5) seconds to a terminal of the CO sensor 106 then the voltage across the C and W terminals of the CO sensor 106 is measured as it returns back to equilibrium over about seven (7) seconds. The equilibrium voltage is about 0.3 volts and then jumps to over 3 volts after the sink current pulse of about −2.1 microamperes.

Figure 3:
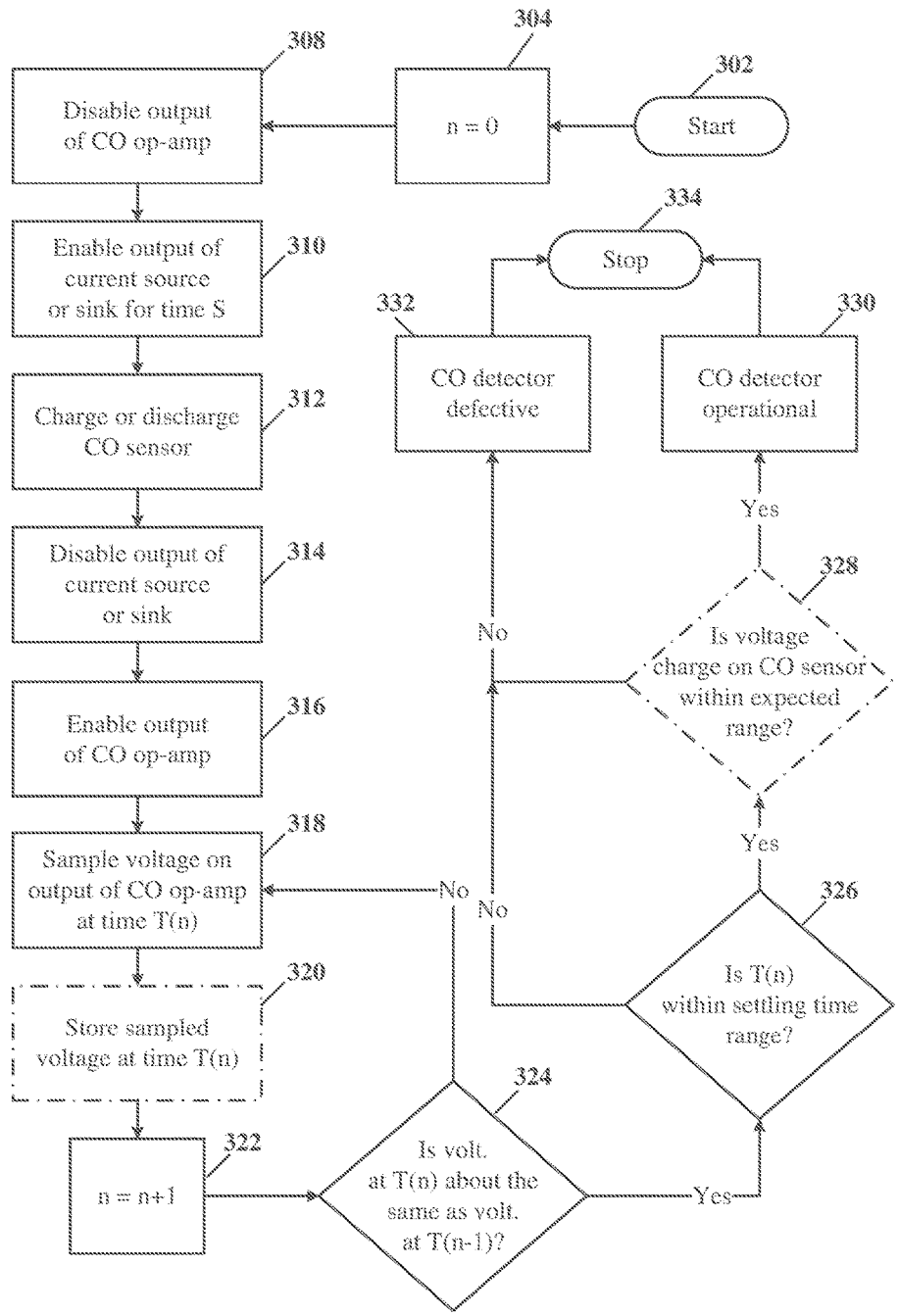
FIGS. 3 and 4 illustrate schematic program flow diagrams for carbon monoxide alarm supervision, according to specific example embodiments of this disclosure.
Figure 4:
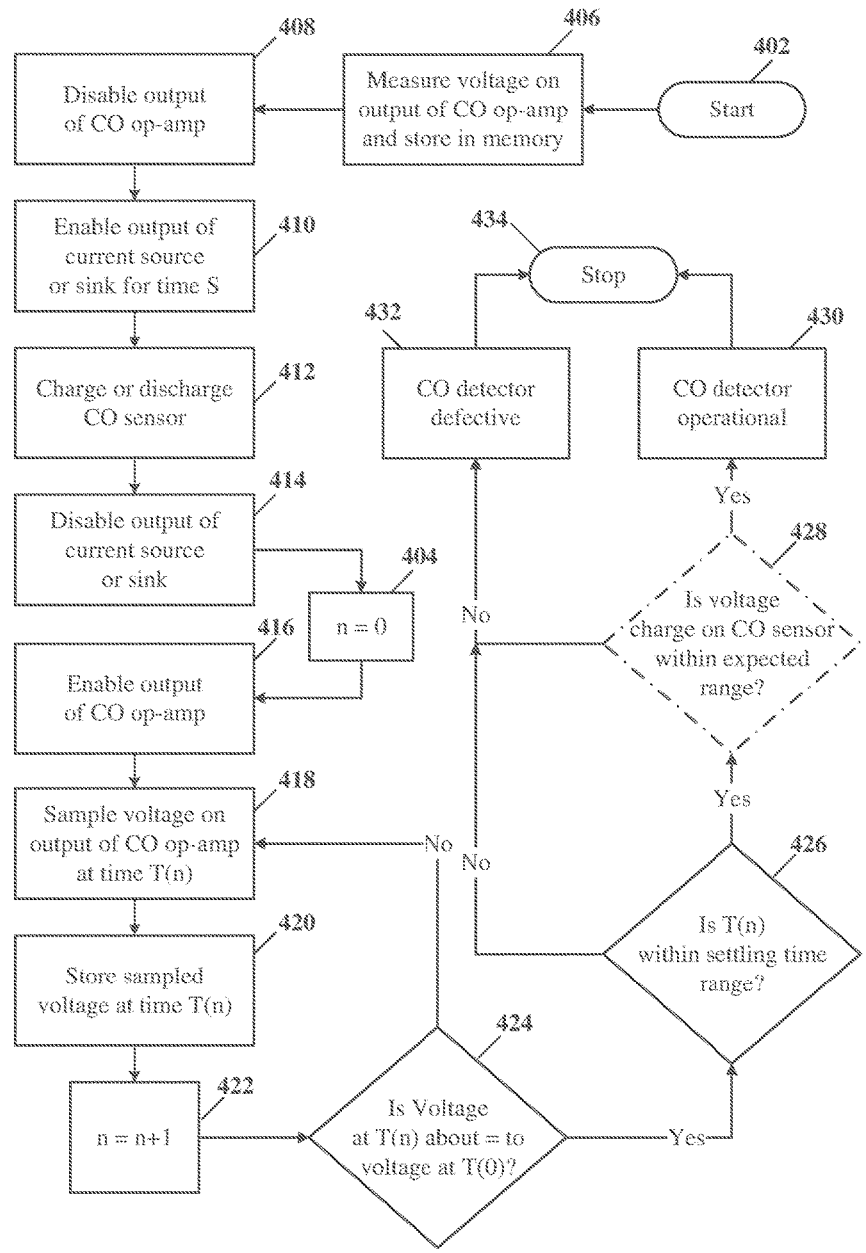

Referring now to FIGS. 3 and 4, depicted are schematic program flow diagrams for carbon monoxide alarm supervision, according to specific example embodiments of this disclosure. A current source or sink pulse unbalances the voltage equilibrium of the CO sensor 106 after the output of the CO operational amplifier 114 has been disabled. Then the CO operational amplifier 114 output is reenabled and the change in voltage charge across the C and W terminals of the CO sensor 106 is observed over time. A properly operating CO detector will have a characteristic voltage/time response when rebalancing a voltage charge back to equilibrium after a current pulse is applied to its CO sensor 106.

FIG. 3 shows a schematic program flow diagram for altering the voltage charge of the CO sensor 106 with the current source/sink 116 and/or current source/sink 118 and then measures the output voltage of the CO operational amplifier 114 over time while characterizing the re-establishment of voltage charge equilibrium on the electrochemical CO sensor 106. Step 302 starts the test process. Step 304 sets a sample count number, n, to zero (0). Step 308 disables the output of the CO operational amplifier 114. Step 310 enables a current source or sink 116 or 118 for a time S. In step 312 the voltage charge on the CO sensor 106 is either charged or discharged by the current source or sink 116 or 118, causing the voltage charge thereon to become unbalanced. In step 314 the current source or sink 116 or 118 is disabled, thus haulting the charging or discharging of the CO sensor 106.

In step 316 the output of the CO operational amplifier 114 is re-enable, wherein the closed loop feedback circuit, comprising the CO operational amplifier 114, CO voltage reference 122 and feedback resistor 124; forces the voltage charge on the CO sensor 106 back into equalibrimum, e.g., a quesient voltage value over time. In step 318 a voltage sample at the output of the CO operational amplifier 114 is taken at time T(n), and in optional step 320 that voltage sample at time T(n) may be stored in a memory, e.g., microcontroller memory shown in FIG. 1. In step 322 n is incremented by 1. Step 324 checks if the previous in time voltage sample is about the same value as the present voltage sample. If not, then a next voltage sample is taken in step 318 and stored in step 320. If so, then the voltage charge on the CO sensor 106 has reached equilibrium, and step 326 evaluates the time elapsed T(n) to determine if the quiescent voltage charge state has been reached within an expected time period. An optional further step 328 may be used in determining whether the voltage charge on the CO detector 106 is at an expected value, e.g., measures voltage between terminals C and W of the CO detector 106. If the results for steps 326 and 328 are yes then in step 330 the CO detector 100 has been determined to be operational. If not, the CO detector 100 circuit is defective.

FIG. 4 shows a schematic program flow diagram for altering the voltage charge of the CO sensor 106 with the current source/sink 116 and/or current source/sink 118 and then measures the output voltage of the CO operational amplifier 114 over time while characterizing the re-establishment of voltage charge equilibrium on the electrochemical CO sensor 106. Step 402 starts the test process. Step 406 measures the voltage on the output of the CO operational amplifier 114 (and stores in memory, e.g., of the microcontroller 104). Step 408 disables the output of the CO operational amplifier 114. Step 410 enables a current source or sink 116 or 118 for a time S. In step 412 the voltage charge on the CO sensor 106 is either charged or discharged by the current source or sink 116 or 118, causing the voltage charge thereon to become unbalanced. In step 414 the current source or sink 116 or 118 is disabled, thus haulting the charging or discharging of the CO sensor 106. Step 404 sets a sample count number, n, to zero (0).

In step 416 the output of the CO operational amplifier 114 is re-enable, wherein the closed loop feedback circuit, comprising the CO operational amplifier 114, CO voltage reference 122 and feedback resistor 124; forces the voltage charge on the CO sensor 106 back into equalibrimum, e.g., a quesient voltage value over time. In step 418 a voltage sample at the output of the CO operational amplifier 114 is taken at time T(n), and in step 420 that voltage sample at time T(n) is stored in a memory, e.g., microcontroller memory shown in FIG. 1. In step 422 n is incremented by 1. Step 424 checks if the present voltage sample at T(n) is about the same value as stored voltage value taken in step 406. If not, then a next voltage sample is taken in step 418 and stored in step 420. If yes, then the voltage charge on the CO sensor 106 has reached equilibrium, and step 426 evaluates the time elapsed T(n) to determine if the quiescent voltage charge state has been reached within an expected time period. An optional further step 428 may be used in determining whether the voltage charge on the CO detector 106 is at an expected value, e.g., measures voltage between terminals C and W of the CO detector 106. If the results for steps 426 and 428 are yes then in step 430 the CO detector 100 has been determined to be operational. If not, the CO detector 100 circuit is defective.

The present invention has been described in terms of one or more preferred embodiments, and it should be appreciated that many equivalents, alternatives, variations, and modifications, aside from those expressly stated (e.g., methods of manufacturing, product by process, and so forth), are possible and within the scope of the invention.

What is claimed is:

1. A carbon monoxide alarm having supervision, comprising:
    an electrochemical carbon monoxide sensor having first and second terminals;
    an operational amplifier having first and second inputs coupled to the first and second terminals, respectively, of the electrochemical carbon monoxide sensor, wherein the operational amplifier has an output that can be enabled and disabled, whereby when the output is disabled it is at a high impedance;
    a voltage reference having an output coupled to the first terminal of the electrochemical carbon monoxide sensor and the first input of the operational amplifier;
    a feedback resistor coupled between the output and second input of the operational amplifier;
    a first current source or sink coupled to the first terminal of the electrochemical carbon monoxide sensor and the first input of the operational amplifier for charging or discharging the electrochemical carbon monoxide sensor, wherein the first current source or sink output can be disabled and enabled;
    a multiplexer having inputs coupled to the first and second inputs and the output of the operational amplifier, and an output adapted for coupling to a first analog input of a microcontroller;
    the output of the operational amplifier is coupled to a second analog input of the microcontroller;
    a supervisor alarm controller having control outputs coupled to the multiplexer, operation amplifier and current source, and an input coupled to the microcontroller;
    wherein
        during testing of the carbon monoxide alarm the operational amplifier is disabled, and the first current source or sink is enabled, whereby the output of the operational amplifier provides a voltage to the microcontroller that is representative of a voltage charge between the first and second terminals of the electrochemical carbon monoxide sensor while the voltage charge reaching equilibrium; and during normal carbon monoxide monitoring the operational amplifier is enabled, and the first current source or sink is disabled, whereby the output of the operational amplifier provides a voltage to the microcontroller that is representative of a voltage charge between the first and second terminals of the electrochemical carbon monoxide sensor.

2. The carbon monoxide alarm according to claim 1, further comprising:

a second current sink or source coupled to the second terminal of the electrochemical carbon monoxide sensor and the second input of the operational amplifier for discharging or charging the electrochemical carbon monoxide sensor, wherein the second current sink or source output can be disabled and enabled.

3. The carbon monoxide alarm according to claim 1, further comprising a microcontroller for controlling the first current source or sink, the multiplexer and the supervisor alarm controller.

4. The carbon monoxide alarm according to claim 3, further comprising a memory with the microcontroller for storing voltage and time values.

5. The carbon monoxide alarm according to claim 1, wherein an application specific integrated circuit (ASIC) comprises the operational amplifier, the voltage reference, the first current source or sink, and the multiplexer.

6. The carbon monoxide alarm according to claim 3, wherein the microcontroller comprises the operational amplifier, the voltage reference, the first current source or sink, and the multiplexer.

7. The carbon monoxide alarm according to claim 1, wherein the operational amplifier comprises a tri-state circuit for enabling and disabling the output thereof.

8. The carbon monoxide alarm according to claim 1, wherein the operational amplifier comprises an open collector circuit for enabling and disabling the output thereof.

9. The carbon monoxide alarm according to claim 1, further comprising a switch coupled between the operational amplifier and the feedback resistor and the multiplexer for enabling and disabling the output thereof.

10. The carbon monoxide alarm according to claim 9, wherein the switch is controlled by the supervisor alarm controller.

* * * * *